United States Patent
Jacobs et al.

(10) Patent No.: US 7,108,506 B2
(45) Date of Patent: Sep. 19, 2006

(54) ONE WALL BOIL AND BITE DENTAL TRAY

(75) Inventors: Scott Jacobs, Lakewood, CO (US); Allison J. LeGendre, Bainbridge Island, WA (US)

(73) Assignee: Archtek, Inc., Lakewood, CO (US)

( * ) Notice: Subject to any disclaimer, the term of this patent is extended or adjusted under 35 U.S.C. 154(b) by 342 days.

(21) Appl. No.: 10/650,292

(22) Filed: Aug. 27, 2003

(65) Prior Publication Data

US 2005/0048443 A1    Mar. 3, 2005

(51) Int. Cl.
*A61C 9/00*    (2006.01)
(52) U.S. Cl. .............................. 433/37; 433/45; 433/80
(58) Field of Classification Search ................... 433/34, 433/37, 45, 80; 128/859, 860, 861, 862
See application file for complete search history.

(56) References Cited

U.S. PATENT DOCUMENTS

| | | | | |
|---|---|---|---|---|
| 1,406,492 A | * | 2/1922 | Vincent | 433/45 |
| 2,696,046 A | * | 12/1954 | Peyton | 433/35 |
| 3,064,354 A | * | 11/1962 | Pos | 433/71 |
| 3,303,844 A | * | 2/1967 | Johnson et al. | 128/862 |
| 3,765,092 A | * | 10/1973 | Neuwirth | 433/47 |
| 4,401,616 A | * | 8/1983 | Wagner | 264/138 |
| 4,413,979 A | * | 11/1983 | Ginsburg et al. | 433/41 |
| 5,026,278 A | * | 6/1991 | Oxman et al. | 433/41 |
| 5,562,449 A | * | 10/1996 | Jacobs et al. | 433/215 |
| 6,860,736 B1 | * | 3/2005 | Allred et al. | 433/80 |
| 6,884,426 B1 | * | 4/2005 | Sagel et al. | 424/401 |
| 6,896,515 B1 | * | 5/2005 | Cozzi | 433/37 |
| 6,896,518 B1 | * | 5/2005 | Jacobs et al. | 433/215 |

* cited by examiner

*Primary Examiner*—Ralph A. Lewis
(74) *Attorney, Agent, or Firm*—John S. Munday

(57) ABSTRACT

A dental tray having a planar portion and a single wall, useful for dental treatments including bleaching, fluoride applications, desensitizing teeth, antibacterial treatments and other dental operations. At least one groove or bead, either continuous or segmented, divides the planar portion into a first planar portion and a second foldable portion inside the tray that can be raised by the patient to form an inner wall after the tray has been inserted into the patient's mouth. The tray is formed from any dental tray material. Preferred are copolymer formed from ethylene and vinyl acetate having a forming temperature between 125° F. and 135° F. and a freezing point between about 80° F. and 106° F.

12 Claims, 3 Drawing Sheets

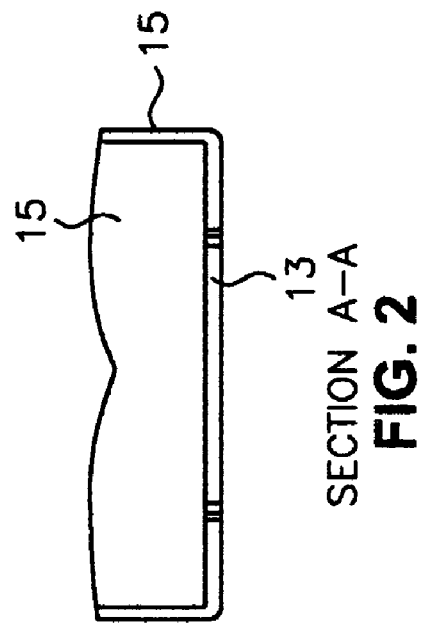
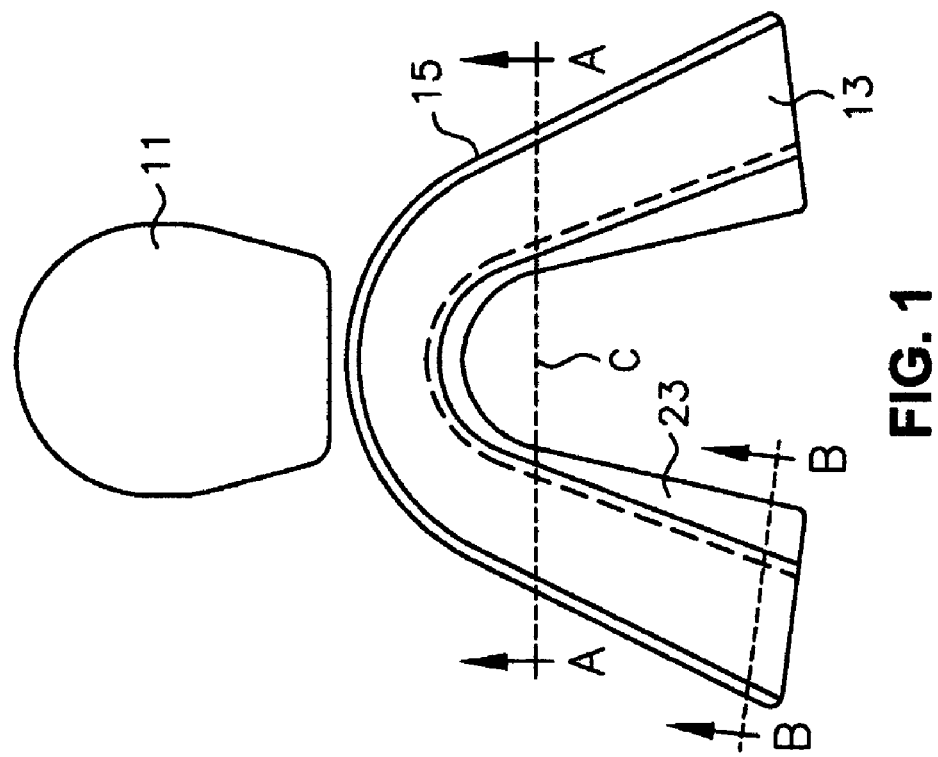

DETAIL B-B

ONE WALL BOIL AND BITE DENTAL TRAY

FIELD OF THE INVENTION

The present invention relates to making a dental tray customized to an individual patient's teeth, without the necessity of a professional's service. More particularly, the present invention relates to a dental tray that can be sized and shaped for a patient with the use of boiling water to soften and form the tray.

BACKGROUND OF THE INVENTION

Dental trays are receptacles that are used to carry a medicine or dental hygiene materials, such as bleaching agents or fluoride application, and apply them to the teeth. It confines the material next to the teeth during the application.

The invention disclosed in U.S. Pat. No. 5,076,791, uses ethylene vinyl acetate and creates a customized dental tray. The resultant tray is so thick that it may cause discomfort. Additionally, it is not hard at normal temperatures and gives less than a custom fit.

Finally, U.S. Pat. No. 5,616,027 discloses a hard, thin dental tray, suitable for many types of dental and at home procedures and uses. The patent uses ethylene vinyl acetate for an outer, non-impression forming tray that can be softened using boiling water. The thin inner tray is customizable to the same accuracy as more expensive custom trays created on a model, but at a fraction of the cost in time, professional expertise or equipment. The inner tray is principally made of a composition of polycaprolactone polymer with co-polymers and additives. The thin dental trays can be customized and molded in the home or outside of a dental office. The problem with this prior art tray and all the others of similar design is that it uses a polymer that can not be shaped at warm temperatures but requires higher temperatures to form, such as when the tray is heated in boiling water.

Since the early 1960s, there have been trays formable by the use of boiling water, which is far too hot for use with a patient. When the tray cools to a usable temperature, the window of pliability and comfort is so small that either the patient experiences discomfort or a bad fit is achieved.

Another industry where hot melting of thermoplastics is the athletic mouthguard industry. U.S. Pat. No. 3,312,218 teaches a protective mouthpiece that can be softened with boiling or near boiling water, then cooled to a temperature and formed in situ by the user. It has been found that a person normally can tolerate a thermoplastic at a temperature of less than 160° F. With a mouthguard, the fit is not as critical as it is with a dental tray but there is another important difference between mouthguards and dental trays. Specifically, mouthguards are thick and hold the heat longer, allowing the user to adjust the shape and fit over a longer period of time than is possible with the thinner and therefore faster cooling dental trays. Thus the window of time and temperature is much smaller for dental trays.

At the present time, the only available dental trays are those which include a front wall and a back wall, with a horseshoe or U-shaped trough in which the treating agent is placed. These two-wall trays are limited in length and wall height because of the requirements when placing the tray in a patient's mouth.

One embodiment of the present invention is the formation of a dental tray that has only one outer labial front wall, thus permitting it to be inserted into a patient's mouth without the obstruction of an inner (lingual) wall.

Another embodiment is to provide a flexible joint on the bottom or planar portion of the tray that can be raised or lifted by the patient, preferably using its tongue, to form an inner (lingual) wall after insertion.

Other embodiments will appear hereinafter.

SUMMARY OF THE INVENTION

The present invention is a dental tray having a planar portion and a single front labial wall, useful for dental treatments including bleaching, fluoride applications, desensitizing teeth, antibacterial treatments and other dental operations. The dental tray of this invention may be used on either the upper or lower teeth. The tray of this invention may be used after changes in the teeth by reheating and redoing the forming process disclosed, in a much more effective and efficient manner than heretofore possible in the dental art.

The planar portion is U-shaped and includes an inner edge and an outer edge. A wall is formed on the outer edge and is designed to confront the front or outer surfaces of the patient's teeth. The inner edge includes a foldable portion that can be raised to form an inner wall once the tray device is warmed in hot water and placed in position in the mouth. A groove or bead, either continuous or segmented, is formed to assist in directing the folding at a predetermined location on said planar portion. A second bead or groove may also be employed to give a raised element for the tongue of the patient to push on to assist in forming the raised portion in the mouth.

Preferred are copolymer formed from ethylene and vinyl acetate having a forming temperature between 125° F. and 135° F. and a freezing point between about 80° F. and 106° F.

DESCRIPTION OF DRAWINGS

FIG. 1 is a plan view showing the dental tray device according to the present invention;

FIG. 2 is a cross-sectional view of the device taken along lines A—A of FIG. 1;

DETAILED DESCRIPTION OF THE INVENTION

Figure 4:
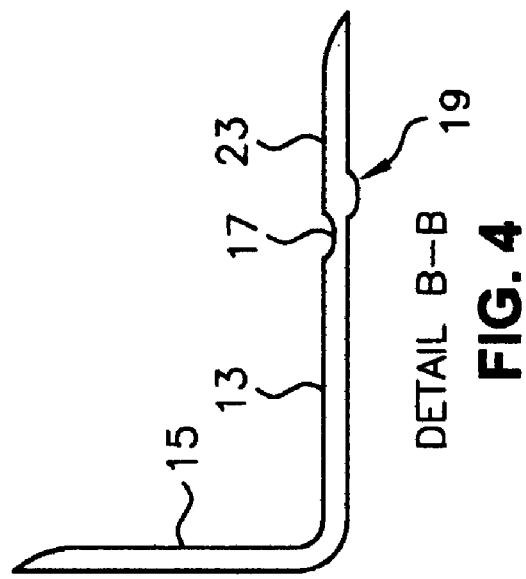
FIG. 4 is a cross-sectional view of the device taken along lines B—B of FIG. 1.
Figure 3:
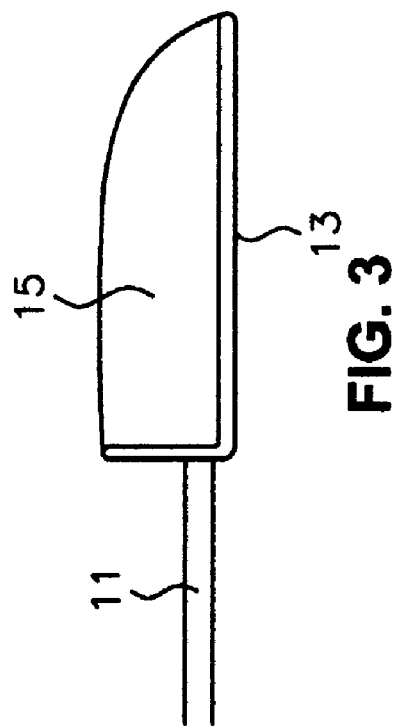
FIG. 3 is a side elevational view of the device shown in FIG. 2, as seen from reference point C of FIG. 1.

In its simplest form the dental tray of this invention is made from an ethylene vinyl acetate copolymer having a forming temperature between 115° F. and 145° F. The copolymer is sized to generally to cover a patient's upper or lower teeth, and thus come in different shapes and sizes to accommodate different patients. The tray is conformed to the teeth at the forming temperature by applying pressure on the tray against the teeth. A preferred temperature is between about 125° F. and 135° F.

As shown in the drawings, the preferred embodiment of the present invention is a one wall dental tray, 10 generally. The device has a tab 11 for holding the tray as it is inserted into a patient's mouth, not shown. The device includes a flat or planar portion 13 and one raised wall 15. Unlike prior art trays, there is no inner or lingual wall, so it is much easier to slide into the mouth without the possibility of having the inner wall fold over, since it is nonexistent.

The tray of this invention also includes one or two fitting aids to assist in helping the patient fold a portion 23 of flat portion 13 up and in contour relationship to the back teeth once the device has been placed in the mouth of the patient. In FIG. 4, a continuous groove 17 is formed on the top of portion 13, separating the portion 23 from the rest of the planar surface 13. Alternatively or in addition, a continuous bead or half round 19 is formed on the underside of portion 13, proximate the region where portion 23 is to be found. Thus the patient can cause portion 23 to be raised up against the back of his or her teeth, forming a more complete tray capable of holding a treating agent such as bleach, fluoride treatment, dental wax for impressions, and the like.

Figure 5A:
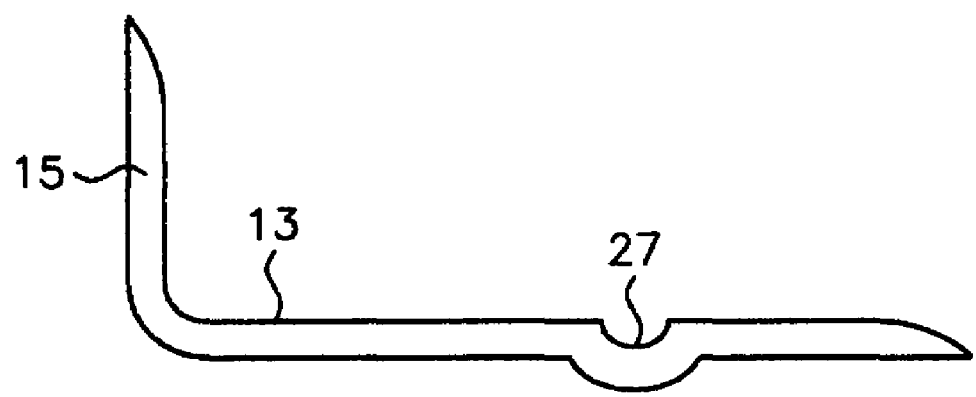
FIGS. 5A, 5B and 5C are cross-sectional views showing alternative embodiments of the dental tray device of FIG. 4.
Figure 5B:
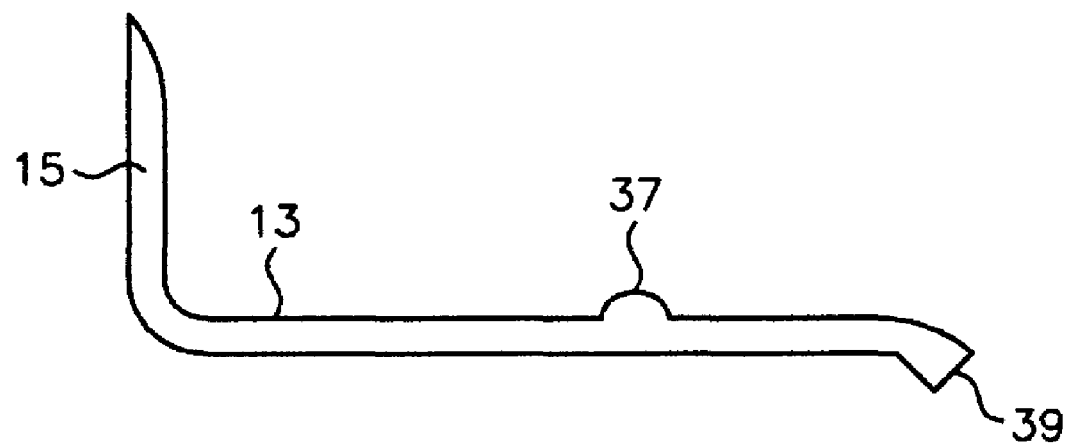
Figure 5C:
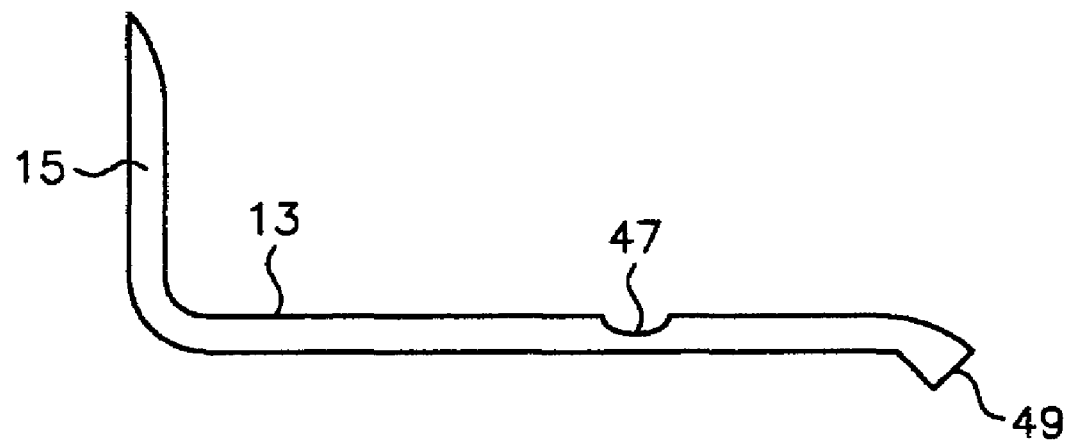

As noted above, the tray of the present invention may have a groove 17, or a bead 19, or both. In FIGS. 5A–5C, alternative embodiments are shown in which groove 27, 37 and 47 are illustrated. Similarly, beads 29, 39 and 49 are alternative embodiments. Any combination of one or both of these embodiments is contemplated by the present invention.

Additionally, the grooves 17, 27, 37 or 47 and beads 19, 29, 39 and 49 may be continuous or segmented, depending on design choice. All that is necessary to form the tray of this invention is to provide some means for permitting the patient, or a dental attendant, to fold the portion 23 into a proximate vertical orientation to contour portion 23 to the back of the teeth.

The present invention permits the use of thin material, with a preferred range of thickness of wall 15 ranging from 0.01 to 0.04 inches, although other thicknesses work also. A nominal thickness of 0.025 inches is most preferred.

Because there is no inner or lingual wall, the tray planar portion 13 and wall 15 can be longer than heretofore possible to provide a longer, more complete coverage tray.

The tray of this invention may be formed from a variety of the commercially available copolymers of ethylene and vinyl acetate, preferably where the percent by weight vinyl acetate is at least 25% by weight. Most preferred are copolymers of ethylene and vinyl acetate in which the percent by weight vinyl acetate is between 25% and 35% by weight. Similarly, the ethylene vinyl acetate copolymer should have a freezing point at which it is not deformable of less than 120° F., and preferably between about 80° F. and 106° F.

In a preferred embodiment, the copolymer is a mixture of two copolymers of ethylene vinyl acetate, each of the copolymers having different forming temperatures between 115° F. and 145° F., the different forming temperatures being at least 25° F. apart. For example, one of the copolymers could have a forming temperature of about 117° F. and a freezing temperature of about 81° F. and the other of the copolymers could have a forming temperature of about 145° F. and a freezing temperature of about 106° F. Most preferred are copolymers that combine to produce a tray having a forming temperature between about 125° F. and 135° F.

Preferred ethylene vinyl acetate copolymers are manufactured by the DuPont Company under the trade name Elvax® ethylene vinyl acetate copolymer. Elvax® is a registered trademark of the DuPont Company. Preferred Elvax® copolymers are designated with a grade designation of Elvax® 150 and Elvax® 240. Presented below is a table showing some of the properties of the preferred materials.

TABLE I

| Elvax ® Grade | Vinyl Acetate | melting pt | freeze pt. |
|---|---|---|---|
| 150 | 33% | 145° F. | 106° F. |
| 240 | 28% | 165° F. | 118° F. |

It is also contemplated at other polymers and copolymers may be added to the formulation of the tray, such as, by way of example and not as a limitation, small quantities of ultra-low density polyethylene or polycaprolactone. The amount may range from about 2% by weight to about 20% by weight, with a preferred range of between about 5% and 10% by weight. Other conventional tray materials may also be used, as long as the material is flexible enough to fold under pressure along a groove 17 or bead 19, as described above.

The tray is now ready for use. While particular embodiments of the present invention have been illustrated and described, it is not intended to limit the invention, except as defined by the following claims.

The invention claimed is:

1. A dental tray for treating a patient's teeth by contacting all the teeth on one jaw, comprising:
   a planar portion having a generally U-shaped configuration surrounding said all the teeth on one jaw with an inner edge and an outer edge; said planar portion having a first portion for holding a treating agent and a second foldable portion on said inner edge;
   a single outer vertical wall fixed in position on the outer edge of said planar portion to confront the front or outer surfaces of the patient's teeth; and
   an element formed proximate the junction of said planar portion and said foldable portion for guiding the folding of said planar portion to raise said foldable portion into an interior tray wall.

2. The tray of claim 1, wherein said element is a groove formed at said junction.

3. The tray of claim 1, wherein said element is a bead formed at said junction.

4. The tray of claim 1, wherein said element is formed on the underside of said planar surface for engagement by a patient's tongue.

5. The tray of claim 4, wherein said element is formed on the upper side of said planar surface for locating said folding portion.

6. The tray of claim 1, wherein said tray is formed from an ethylene vinyl acetate copolymer having a forming temperature between 115° F. and 145° F.

7. A dental tray for treating a patient's teeth by contacting all the teeth on one jaw, comprising:
   planar portion means for forming said tray and having a generally U-shaped configuration surrounding said all the teeth on one jaw with an inner edge and an outer edge; said planar portion means having a first portion for holding a treating agent and a second foldable portion on said inner edge;
   wall means for forming a single outer vertical wall fixed in position on the outer edge of said planar portion means to confront the front or outer surfaces of the patient's teeth; and
   junction means for forming the junction of said planar portion and said foldable portion for guiding the folding of said planar portion to raise said foldable portion into an interior tray wall.

8. The tray of claim 7, wherein said junction means is a groove formed at said junction.

9. The tray of claim 7, wherein said junction means is a bead formed at said junction.

10. The tray of claim 7, wherein said junction means is formed on the underside of said planar surface for engagement by a patient's tongue.

11. The tray of claim 10, wherein said junction means is formed on the upper side of said planar surface for locating said folding portion.

12. The tray of claim 7, wherein said tray is formed from an ethylene vinyl acetate copolymer having a forming temperature between 115° F. and 145° F.

* * * * *